United States Patent [19]

Miller et al.

[11] Patent Number: 4,659,738

[45] Date of Patent: Apr. 21, 1987

[54] TOPICAL PROPHYLAXIS AGAINST SCHISTOSOMAL INFECTIONS

[75] Inventors: Robert E. Miller, Gaithersburg; Willis A. Reid, Jr., Bethesda, both of Md.

[73] Assignee: The United States of America as represented by the Secretary of the Army, Washington, D.C.

[21] Appl. No.: 702,114

[22] Filed: Feb. 15, 1985

[51] Int. Cl.⁴ .................... A61K 31/21; A61K 31/165
[52] U.S. Cl. .................................... 514/514; 514/619; 514/622
[58] Field of Search ........................ 514/622, 514, 619

[56] References Cited

U.S. PATENT DOCUMENTS 4,173,632 11/1979 Cruthers et al. .................... 514/622

FOREIGN PATENT DOCUMENTS 2043107 12/1975 Japan ................................... 514/622
1050767 12/1966 United Kingdom ................ 514/622

*Primary Examiner*—Frederick E. Waddell
*Attorney, Agent, or Firm*—John H. Raubitschek; Francis A. Cooch; Werten F. W. Bellamy

[57] ABSTRACT

An improved method is provided for the prevention of schistosomal infections in animals. The topical application of a 2-hydroxy-benzoic anilide provides prophylactic protection against penetration by infective cercariae of the parasitic worms.

31 Claims, No Drawings

TOPICAL PROPHYLAXIS AGAINST SCHISTOSOMAL INFECTIONS

BACKGROUND OF THE INVENTION

Schistosomal infections are caused when infected fresh or salt water snails shed free swimming infective larval parasites (cercariae) into the water which infect both animals and humans by the penetration of the parasite through their skin. The penetration of the skin by the parasites can result in infections ranging from skin infection (schistosome cercarial dermatitis or swimmer's itch) to schistosomiasis.

Cases of schistosome cercarial dermatitis have been reported from many regions of the United States, Australia, Europe, Central and South America, Africa, India, New Zealand, Japan, Malaya and Thialand. The schistosomes which are responsible for the major reports of fresh water cercarial dermatitis belong to the genera Trichobilharzia, Ornithobilharzia, and Schistosoma. Microbilharzia spp. cercariae have been identified as the major cause of cercarial dermatitis along salt water beaches of California, Connecticut, Florida, Hawaii, and Rhode Island. Various schistosome species belonging to the genera Schistosomatium, Austrobilharzia, Gigantobilharzia, Heterobilharzia, Orientobilharzia, Ornithobilharzia and Trichobilharzia, as well as Schistosoma and Microbilharzia have been implicated in causing cercarial dermatitis.

Schistosomiasis (also known as bilharziasis, is a state of infection with parasitic flat worms (trematodes) belonging to one or more species of blood flukes of the family Schistosomatidae. Schistosomiasis is the most important among parasitic diseases caused by worms. An estimated 200 million people are infected by blood flukes in regions of Asia, Africa, South America, and also the Caribbean area. The human disease complex results from infection by three major species of digenetic trematodes, viz., *Schistosoma mansoni, S. japonicum,* and *S. haematobium.* Other schistosome species, notably *Schistosoma mekongi, S. intercalatum, S. bovis, S. rodhaini, S. spindale, S. mattheei, S. margrebowiei, Schistosomatium douthitti* and *Heterobilharzia americana* are also known to establish human infections. Fundamentally, an infected fresh water snail sheds free swimming infective forms (cercariae) into the water, and man (or other animal) is infected by the penetration of the parasite through the skin, followed by maturation of the worms (male and female) in the body, pairing of male and female worms, shedding of eggs in excrement into water; host snails are then invaded by larvae (miracidia) for continuation of the cycle. In the animal host, the schistosomes enter the blood circulation and pass through the lungs to mature in the liver, then reside in mesenteric-portal or pelvic blood circulatory systems. Eggs are laid by the female worm and migrate into the lumen of the small intenstine in the case of *Schistosoma japonicum* and *S. mansoni* or the bladder in the case of *S. haematobium* and, rarely, *S. mansoni.* Most of the pathological effects resulting from schistosomal infections derive from the spined eggs, both within the body and in being shed in the uninary or fecal stream. Specific primary clinical problems occur in the intestine and bladder, together with seconary ones in liver, spleen, and lungs, plus variable involvement of the central nervous system and retina. The worms may live for many years and the immune response of the host has little effect on established adult schistosomes, but may work against development of new infections. Pathological changes in schistosomiasis are considerably variable with the species and strain of parasite and are influenced by such factors as duration of the infection, intercurrent infections, and nutritional state of the animal host.

Treatment of the schistosomiases does not reverse the damage already done the animal host by the parasite worms. Anti-schistosomal agents generally impair the production of eggs and hinder development and functions of the flukes, with or without actually killing them. "Cure" is said to be achieved when viable eggs are no longer found in the excrement. It should be understood that such criterion does not imply absence of worms. Successful treatment of the schistosomiases is difficult to achieve safely, for anti-schistosomal agents are appreciably toxic to the host. Suppressive management of schistosomiasis through administration of drugs at regular intervals may also be hazardous to the patient. Treatment of the infections is increasingly difficult in the sequence: *Schistosoma haematobium, S. mansoni,* and *S. japonicum.* That is essentially the same as the general extent of severity of the consequences of those schistosomes.

Control of schistosomiasis through interruption of the life cycle of the parasite is a more attractive course of action than treatment of the infection. Two points at which control may be exercised are eradication of the snail intermediate host and prevention by protection of the animal host against the cercariae shed by the snails. Various means have been tried to eliminate snails, for example, mollscicides and biological control measures. However, the basic problems have not been solved and even 0.2% of a snail population being infected renders a region highly endemic to schistosomiasis.

The use of a wide variety of topically applied prophylactics to prevent infection by human schistosome cercariae has been comprehensively reviewed by Pellegrino in *Experimental Parasitology,* Vol. 21, pages 112 to 131 (1967). Since this review, however, only a few topical prophylactic agents have been evaluated by Gilbert et al., in the *Journal of Parasitology,* Vol. 56, pages 397-398, (1970); Austin and Frappaolo, in the *American Journal of Topical Medicine and Hygiene,* Vol. 22, pages 743 to 747, (1973); and Greene et al., in the *American Journal of Tropical Medicine and Hygiene,* Vol. 32, pages 1356 to 1363, (1983). Prior to applicants' invention, the most effective topical cercarial antipenetrants reported by other investigators appear to have been bithionol and hexachlorophene (Kemp et al., *Military Medicine,* Vol. 119, pages 1 to 10, 1956; and Campbell and Cuckler, *American Journal of Tropical Medicine and Hygiene,* Vol. 10, pages 712 to 715, 1961).

Niclosamide, for example, and its ethanolamine salt have been widely used as both a molluscicide and a cercaricide to control *Schistosoma mansoni* when applied to infested waters at concentrations as low as 0.1–0.2 mg/l (Webbe, *Bulletin of the World Health Organization,* Vol. 25, pages 525 to 531, (1961)). However, there have been no published scientific studies of niclosamide describing its use as a topical antipenetrant. In our study it did not cause any observable dermal reaction, did not discolor the skin, and resisted removal by water washing.

SUMMARY OF THE INVENTION

Prevention of schistosomal infections involves protection of man or other animal host against infection by cercariae of the trematodes. In this regard, it would be desirable to have perdurable topical agents which, when applied to the skin, could afford means of safely preventing schistosomiasis. Prior to applicants' invention, this goal had not been achieved. It is known that various agents, when applied topically, provide some extent of protection of an animal host against infection by penetration of the cercariae of Schistosoma mansoni or S. japonicum. On the practical assessment of the results, however, the protective effects decrease markedly if the skin surface is washed or exposed to running water. Therefore, such topical agents offer little advantage if used by personnel (civilian or military) who may be exposed to waters containing schistosome-infected snails. Practical utility of a topical anti-penetrant should include: resistance to washing action of flowing water, lack of irritant characteristics to the skin, ease of application, and low cost.

Accordingly, it is an object of this invention to provide topical chemoprophylactic agents useful in the prevention of schistosomal infections.

It is another object of the invention to provide topical agents which are resistant to the washing action of flowing water.

It is another object of the invention to provide topical agents which are non-irritating when applied to the skin.

It is another object of the invention to provide topical agents which are inexpensive and easy to apply.

Yet other objects of the invention will become apparent to one of ordinary skill upon reading this disclosure.

The above objects are achieved by the method of this invention for preventing schistosomal infections in an animal which comprises applying to the skin of said animal a composition which contains a 2-hydroxy-benzoic anilide represented by the formula:

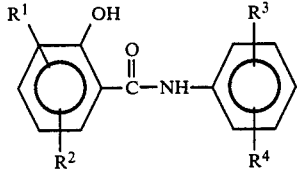

wherein $R^1$ is hydrogen or halogen; $R^2$ is $NO_2$ or halogen (including Cl, Br, F and/or I); $R^3$ is hydrogen, halogen (including Cl, Br, F and/or I), alkyl (having 1 to 3 carbon atoms),

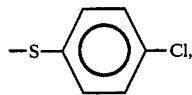

$CF_3$; and $R^4$ is $NO_2$, —NCS, or $R^3$. It is essential that the 2-hydroxy-benzoic anilide compounds used in the practice of this invention contain at least one elecrophilic group on either phenyl ring. For topical application of the 2-hydroxy-benzoic anilide compounds of this invention may be dissolved in any physiologically-acceptable vehicle in order to achieve an antipenetrant effect against cercariae of infectious schistosome parasites.

The present invention relates to novel means for protecting animals against infection by cercariae of infectious schistosome parasites. It is based upon preventing access of cercarial forms of the worms through the skin by topical application of compositions containing a 2-hydroxy-benzoic anilide antipenetrant agent.

These novel antipenetrants are nontoxic and nondiscoloring to the skin, and are more resistant to removal by water washing than other compositions. Evidence indicates that they are effective in barring entry of the cercariae of the various Schistosoma species.

The antipenetrant agents used in the practice of this invention offer safe, easy, and inexpensive means for protection of civilian populations and military troop personnel against infection by schistosomes as will be apparent from the detailed description below.

DETAILED DESCRIPTION OF THE INVENTION

The compositions of the invention may be applied to the skin by any suitable means for protecting against penetration by cercariae of schistosome worms. Exemplary vehicles for achieving uniform application include: solutions (as, an alcoholic solution i.e. methanol, ethanol, or isopropanol); dimethylsulfoxide; creams (as, vanishing cream); ointment (as, white or yellow ointment); liniment (as, green soap tincture); or malagma (as an emollient oil). The antipenetrant may remain on the skin for hours without decrease in effectiveness and without irritation, and exposure to flowing water will not readily remove the agent. Accordingly, persons who are protected by the method of this invention may be exposed to schistosome-infested waters, whether for civilian or military purposes, with minimal hazards of skin penetration by cercariae of the worms.

The concentration of antipenetrant agent (drug) in the composition is from about 0.10% to about 3.0% weight of drug/volume of vehicle (w/v). In general, of course, lower concentrations have an advantage from the standpoint of economics and lack of irritation. Hence, a more preferred range of concentration of antipenetrant agent in the composition is from about 0.5% to about 1.25% weight of drug/volume of vehicle (w/v). The most preferred range is 0.9% to 1.1%.

This invention relates to a method for preventing schistosomal infections, including schistosomiasis and schistosome cercarial dermatitis (swimmer's itch), in an animal exposed to schistosome-infested water which comprises applying to the skin of said animal prior to exposure to the schistosome-infested water a composition comprising an effective amount of a 2-hydroxy-benzoic anilide selected from the compounds represented by the formula:

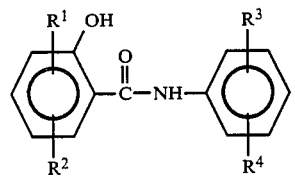

wherein $R^1$ is hydrogen or halogen (including Cl, Br, F and/or I); $R^2$ is $NO_2$ or halogen (including Cl, Br, F and I); $R^3$ is hydrogen, hydroxy, halogen (including Cl, Br, F and/or I), alkyl (having 1 to 3 carbon atoms),

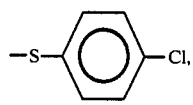
$CF_3$; and $R^4$ is $NO_2$, —NCS, or $R^3$ in an amount sufficient to achieve an antipenetrant effect against cercariae of infectious schistosome parasites. Representative 2-hydroxy-benzoic anilide include compounds having the following chemical formula:
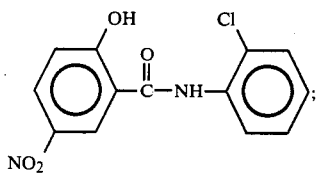
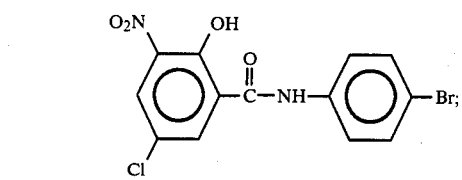
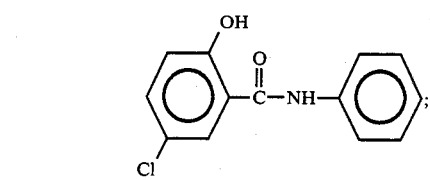
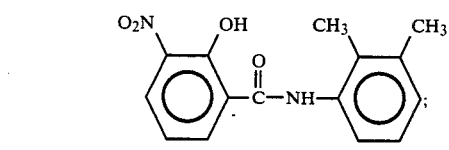
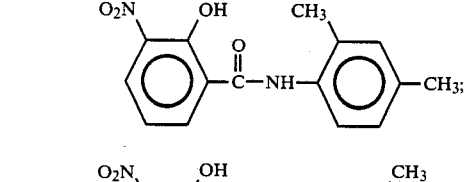
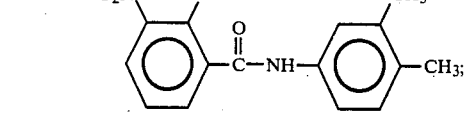
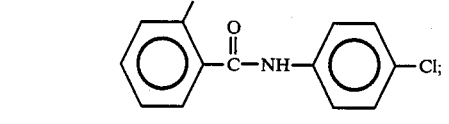
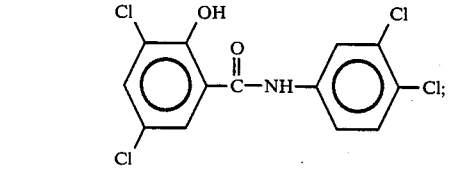
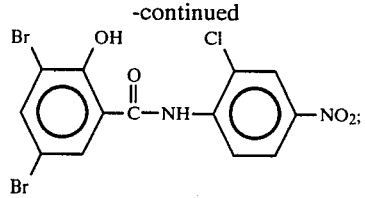
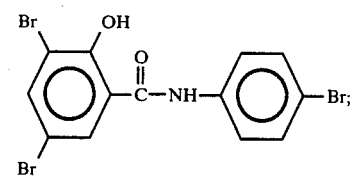
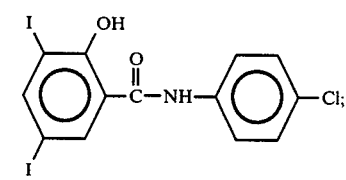
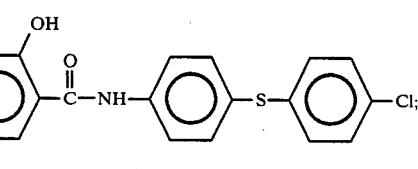
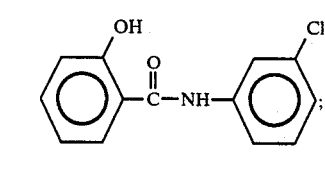
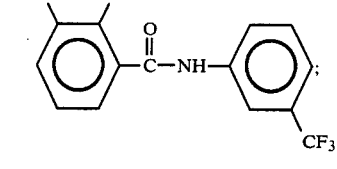
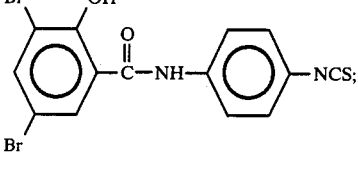
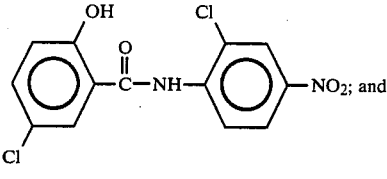
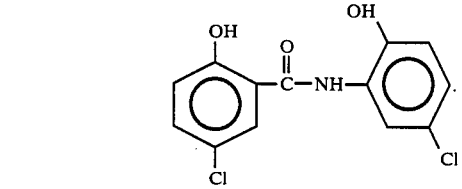

EXAMPLES

The examples set forth below illustrate, without any implied limitation, and salient features of laboratory tests which lead to the conclusion that 2-hydroxy-benzoic anilides are useful in providing prophylactic protection against penetration of infective cercariae of parasitic worms.

Procedure, Materials and Methods

Procedure (Schistosomiasis Evaluation)

Salicylanilide and 38 of its analogs were tested on mice as potential topical chemoprophylactic agents against Schistosoma mansoni cercariae penetration in mice. The compounds were solubilized in absolute methanol, ethanol, dimethyl sulfoxide, or isopropanol at concentrations not exceeding 1.25 percent w/v. The tails of each of the ten mice per group were treated by immersion in 5 ml of the test compound solution or of vehicle control alone. From each group, the treated tails of 5 mice were washed for 30 minutes in flowing tap water 3 to 4 hours after compound application. All mice were exposed to approximately 100 cercariae 24 hours after treatment. The mice were perfused 49 days post-exposure and worm burdens were determined. The protective capacities of each compound were calculated by measuring the reduction of the worm burdens of the compound treated mice compared to those treated with the vehicle only, and expressing the resulting value as percent protection. Of the 39 compounds tested, 21 provided 98 percent or better protection if the treated tails were not washed before exposure to cercariae. Of these 21 active compounds, 17 of them still provided 98 percent or better protection from infection by S. mansoni cercariae even after the mouse tails were subjected to a 30-minute wash test.

Chemicals

The Walter Reed Numbers (WR) and chemical structure relationships of these compounds are shown in Table I.

All compounds were tested for solubility in all of the following organic vehicles: methanol (Fisher Chemical Co., Fair Lawn, NJ), dimethyl sulfoxide (Fisher Chemical Co., Fair Lawn, NJ), isopropanol (Fisher Chemical Co., Fair Lawn, NJ), or ethanol (Publick Chemical Co.). The vehicle to be used depended upon the solubility of the compound. The concentration of each compound used in each experiment was 1.0 or 1.25 percent, or if they were not soluble at 1.25 or 1 percent they were used at their maximum solubility at room temperature.

Test Treatment

In this study, 17–23 gram male mice (WRAIR colony, outbred Charles River ICR strain) were used in all experiments. The mice were treated, in groups of ten mice each, with either the vehicle alone or the vehicle containing the test compound according to a modified method described by Greene et al. in the *American Journal of Tropical Medicine and Hygiene*, Vol. 32, pages 1356 to 1363 (1983). The tail of each mouse was treated by dipping it into 5 ml of the appropriate test compound for 5 minutes in 13 mm × 100 mm disposable culture tubes secured in a medium Loyd Board (Bruce and Radke, *Biomedical Report*, Vol. 19, 406th Medical Laboratory, Part I, pages 1 to 84, 1971). The mice were immobilized in WRAIR mouse restrainers as described by Radke et al. in *Experimental Parasitology*, Vol. 30, pages 1 to 10, (1971). After treatment, the tails were allowed to air dry before the mice were removed from the restrainers. The groups of mice were divided again into two groups of five mice each; one group had their treated tails washed while the other did not. At 3–4 hours post-treatment, the mice of the groups to be "washed" were again placed in the restrainers and their tails immersed in running tap water (20°–26° C.) for 30 minutes. Each such group was washed in separate containers at a flow rate of 2–3 liters of tap water per minute.

Mouse Infections

Cercariae (WRAIR, Puerto Rican strain of *Schistosoma mansoni*) were shed en masse from 200–300 infected *Biomphalaria glabrata* snails (WRAIR, albino strain) and exposed to mice within 3 hours of emergence from the snails. All mice were individually exposed to approximately 100 cercariae in 4.5 ml dechlorinated water. The tails of the mice were immersed for one hour in the cercarial suspension as described by Radke et al. *Experimental Parasitology*, Vol. 30, pages 1 to 10, (1971).

All mice were killed 49 days post-exposure by injecting 0.5 ml of heparinized pentobarbital solution (100 units per ml) intraperitoneally. Worm burdens were determined from hepatoportal perfusions. Worms were collected on filter paper discs according to a modified method of Radke et al. *Journal of Parasitology*, Vol. 47, pages 366 to 368, (1961), and Radke et al., *Journal of Parasitology*, Vol. 48, pages 500–501, (1962) using heparinized Ringer's lactate (10 units per ml) as the perfusion solution.

The worms from each perfused mouse were washed off the filter disc into normal saline in 47 mm dishes and total worm counts of male, female, and sexually immature worms were determined.

Calculation of Drug Activity

The protective activity of each compound was calculated as follows:

$$\text{Percent Protection} = 100 \times \left(1 - \frac{TWB \text{ Experimental}}{TWB \text{ Control}} \times \frac{100 \, SmC}{\text{Number of } SmC}\right)$$

used where TWB=Total Worm Burden and SmC=*Schistosoma mansoni* cercariae. The value is thus an indication of the protective capacity of a given test compound relative to the untreated control group and is expressed as "percent protection."

Procedure (Schistosome Cercarial Dermititis Evaluation)

Mangold and Dean, *American Journal of Tropical Medicine and Hygiene*, Vol. 32 (4), pages 785 to 789, (1983) have reported an autoradiographic method to identify radio-labeled cercariae in whole mouse skin. They have reported that greater than 91 percent of the cercariae used for exposure can be determined in the tail skin of naive mice.

The present technique of evaluating the topical prophylactic properties of compounds against schistosomes is the recovery of adult worms 6–7 weeks post-exposure. However, this screening method uses only one concentration of compound and cannot differentiate whether cercariae are prevented from penetration or whether they die post-penetration. The radio-labeled cercariae technique does not only identify compounds which prevent penetration of cercariae, but would also provide important initial dose effect information. Additionally, holding time for mice is reduced to 3 days.

Applicants have found that direct counting of cercariae by audioradiography provided a more accurate picture of the topical prophylactic antipenetrant properties of compounds than does the recovery of adult worms.

This procedure enabled applicants to evaluate the utility of autoradiography of radio-labeled cercariae in the tail or skin of mice. The technique evaluated compounds previously determined to provide either complete protection or no protection at all using the adult worm recovery technique.

Procedure, Materials and Methods

Infectious Materials

EXAMPLE 1

Fifty *Biomphalaria glabrata* snails (WRAIR strain) infected for 7 weeks with a WRAIR-Puerto Rican strain of *Schistosoma mansoni* were individually exposed to 10 micro Ci of [$^{75}$Se] L-selenomethionine (Amersham Corp., Arlington Heights, IL) at a specific activity of 20–50 Ci/mmole for 5 hours (Christenson, *Z. Parasitenkd.*, 54:275–288, 1977). Radio-labeled cercariae were recovered 4 and 6 days later by illuminating the labeled snails with 2–100 W incandescent microscope lamps at 28°–30° C. The snails were shed en masse with gentle aeration.

Compounds

The 2-hydroxy-benzoic anilide compounds (WR593, WR34912 and WR46234 were found to be 100 percent protective by the adult worm perfusion antipenetration screen used in this study.

Each compound tested was diluted 4 fold with a starting concentration of 10 mg/ml (240 mg/24 ml) in absolute ethanol. The dilutions (2.5 mg/ml; 0.625 mg/ml; 0.156 mg/ml and 0.039 mg/ml) were made of each compound. The dilutions were made in Corning 50 ml polypropylene screw cap centrifuge tubes.

The solutions were vortexed between each dilution. Five ml of each dilution was dispensed into three 12×750 mm Neutrex ® culture tubes. On the day of treatment (1 day pre-exposure to cercariae), a total of 15 mice (WRAIR strain ICR male, 20–25 grams) were used for each compound. Three mice were used for each concentration and 10 animals were treated with absolute ethanol as a vehicle control (Greene et al., *American Journal of Tropical Medicine and Hygiene*, Vol. 32 (6), pages 1356 to 1363, (1983)). The animals were restrained (unanesthetized) on a Loyd Exposure Broad (LEB) and their tails were treated by immersion for 5 minutes. (Bruce and Radke, *Biomedical, Report No. 19*, 406th Medical Laboratory, pages 1 to 84, 1971). The mice were removed from the LEB and their tails allowed to air-dry before being removed from the restrainers. The mice were replaced in cages for 2–4 hours before the tail washing procedure. The tails of the mice were washed (using restraint and no anesthesia) by groups, for 30 minutes with flowing tap water (3 liters/minutes at 22°–27° C.) through a 1.6 liter washing cell. After removal from the wash board, the mice were removed from the restrainers and placed in cages with food and water ad libitum.

EXAMPLE 2

The same procedure was followed as outlined in Example 1 except that (1) *Physa gyrina* were substituted for 50 *Biomphalaria glabrata*; (2) *Gigantobilharia huronensis* was substituted for *Schistosoma mansoni*; (3) the cercariae were shed in the dark rather than under 2–100 watt incandescent microscope lamps; (4) WR46234 was used in place of WR593, and WR34912; (5) a 1.0% concentration of the tested compound was used instead of making a 4-fold dilution with a starting concentration of 10 mg/ml; (6) 10 mice were used instead of 15 mice and were anesthetized with pentobarbitol instead of using unanesthetized mice on a Loyd Exposure Board; and (7) and the infection-site was the abdominal skin instead of the tail skin.

Mouse Infection

One day post-treatment, approximately 75±3 (SD) radio-labeled cercariae in 0.75 ml water were pipetted by Selectapette ® into 12×750 mm Neutrex ® culture tubes and the final volume adjusted to 4.5 ml with aerated water. Group I mice on Tuesday and Group II mice on Thursday, as well as 10 untreated infection control mice with each group, were restrained and their tails exposed to cercariae for 1 hour by standard methods. The numbers of non-penetrating cercariae remaining in each tube were counted. The schedule followed is outlined below:

| Day of Week | Day | Schedule Event |
|---|---|---|
| Friday | −4 | Label 50 snails with [$^{75}$Se], 10 micro Ci/each. |
| Monday | −1 | Treated mouse tails with 3 compounds in methanol and washed. |
| Tuesday | 0 | Shed snails and expose Group 1 treated mice and infection control mice. |
| Wednesday | +1 | Collect tail skins from day 0 exposure mice. Treat mice with remaining 3 compounds. |
| Thursday | +2 | Shed snails again and infect Group II treated mice and infection control mice (3 compounds). |
| Friday | +3 | Collect tail skins from +2 mice and set up autoradiographic press. Expose 50 snails to 10 micro Ci each. |

Autoradiographs

The autoradiographic procedure is a slight modification of the technique of *American Journal of Tropical Medicine and Hygiene*, 32 (4), pages 785 to 789, Mangold and Dean (1983). The mice were sacrificed by cervical dislocation 24 hours after exposure to cercariae. Tail skins were removed and mounted flat on cardboard with double adhesive cellophane tape and then covered with a layer of cellophane tape. The card with tissue were dried at 37° C. for 5 hours in a Precision ® gravity convection incubator. X-ray film (SAR-5, Eastman Kodak Co., Rochester, NY) was overlayed on the tissue-containing cards and placed in screw presses. Labeled schistosomula in the mouse tail skins appeared as distinct foci of reduced silver on the developed film. The foci were counted and percentages of penetration presented were calculated.

Results

There were no toxic deaths of the mice as a result of treatment with the vehicles or any of the test compounds. Although some of the drug solutions slightly discolored the skin, there were no apparent toxic or sensitizing dermal reactions to any of the compounds.

The mean number of cercariae used to infect the experimental animal groups was 102.7±2.9 (±1SD) per mouse. The average worm recoveries from the vehicle control mice were not statistically different (Tables II, III, and IV). The average corrected mean worm burden (MWB) for each vehicle was 49.9 for methanol (Table II), 44.3 for dimethyl sulfoxide (Table III), 34.7 for isopropanol (Table IV) and 30.2 for ethanol (Table V), or an overall adult worm recovery from the control mice of 43 percent from a corrected 100 cercariae infection in mice.

Of the 39 compounds tested, 21 of them (WR3216, WR3582, WR13084, WR25817, WR25818, WR25819, and WR78306—Table II); (WR593, WR34912, WR39958, WR39960, WR41252, WR47331, WR52606, WR55787, WR66707, WR78550, WR81231, and WR251250—Table III); (WR46234—Table IV); and (WR96544—Table I) provided 98 percent or better protection if the treated mouse tails were not washed prior to exposure to *S. mansoni* cercariae. The parent compound, salicylanilide (2-hydroxy-benzoic anilide) (WR10019), provided 96.6 percent protection if not subjected to washing pressure, but lost over half of its protection if the mouse tails were washed before exposure to cercariae (46.3 percent protection) (Table III). When the mouse tails were washed for 30 minutes after drug treatment, the number of compounds maintaining 100% protection decreased to 6. The protection afforded by one compound (WR25817) decreased from 100% to 98.3% (Tables II, III, and IV). Only WR10019, WR39960, WR47332, and WR81231 of the above listed compounds exhibited significantly decreased activity as a result of washing.

More significantly, the highest level of protection (greater than 98 percent for mice in the unwashed and washed groups) was afforded by compounds having at least one electrophilic group, usually a halogen, substituted on either phenyl ring (Compounds WR3216, WR3582, WR13084, WR25817, WR25818, WR25819, WR78306, WR593, WR34912, WR 39958, WR41252, WR52606, WR55787, WR66707, WR78550, WR251250, and WR46234). All of the above compounds provided maximum protection even after washing the mouse tails. The electrophilic groups were either a halogen or one nitro group in combination with at least one halogen.

TABLE I

Chemical structure relationships of salicylanilide analogs tested for topical prophylaxis on mice for *Schistosoma mansoni* cercariae

| Walter Reed Number | Structure | Walter Reed Number | Structure |
|---|---|---|---|
| WR593 | 2,4-dichloro-6-hydroxy-benzoic 3,4-dichloroanilide | WR3216 | 2-hydroxy-5-nitro-benzoic 2-chloroanilide |
| WR3582 | 2-hydroxy-4-chloro-5-nitro-benzoic 4-bromoanilide | WR10019 | 2-hydroxy-benzoic anilide (salicylanilide) |
| WR13084 | 2-hydroxy-4-chloro-benzoic anilide | WR17456 | 2-hydroxy-benzoic 4-hydroxyanilide |
| WR25817 | 2-hydroxy-5-nitro-benzoic 2,3-dimethylanilide | WR81231 | 3-hydroxy-2-naphthoic anilide |
| WR81741 | 4-trichloromethyl-benzoic anilide | WR81795 | bis-anilide with pyridyl groups |

TABLE I-continued
Chemical structure relationships of salicylanilide analogs tested for topical prophylaxis on mice for *Schistosoma mansoni* cercariae

| Walter Reed Number | Structure | Walter Reed Number | Structure |
|---|---|---|---|
| WR81800 | 4-F-C6H4-NH-CO-C6H4-CO-NH-C6H4-4-F | | |
| WR81801 | (4-O2N, 2-Br-C6H3)-NH-CO-C6H4-CO-NH-(2-Br, 4-NO2-C6H3) | | |
| WR81802 | (2-H3CO, 5-SO2N(C2H5)2-C6H3)-NH-CO-C6H4-CO-NH-(2-OC3H, 5-SO2N(C2H5)2-C6H3) | | |
| WR81803 | (2-H3CO, 5-SO2NHC4H9-C6H3)-NH-CO-C6H4-CO-NH-(2-OCH3, 5-SO2NHC4H9-C6H3) | | |
| WR25818 | (3-O2N, 2-HO-C6H3)-CO-NH-(2,4-(CH3)2-C6H3) | WR25819 | (3-O2N, 2-HO-C6H3)-CO-NH-(3,4-(CH3)2-C6H3) |
| WR34912 | (3,5-Br2, 2-HO-C6H2)-CO-NH-(4-Br-C6H4) | WR39958 | (3,5-Br2, 2-HO-C6H2)-CO-NH-(2-Cl, 4-NO2-C6H3) |
| WR39960 | (3,5-Br2, 2-HO-C6H2)-CO-NH-C6H4-O-C6H4-Cl | WR41252 | (3,5-I2, 2-HO-C6H2)-CO-NH-(4-Cl-C6H4) |
| WR42406 | (3,5-Br2, 2-HO-C6H2)-CO-NH-C6H4-SO2-C6H4-NH-CO-(2-HO, 3,5-Br2-C6H2) | | |
| WR46234 | (3,5-Cl2, 2-HO-C6H2)-CO-NH-(2-Cl, 4-NO2-C6H3) | WR47332 | (3,5-Br2, 2-HO-C6H2)-CO-NH-C6H4-CO-C6H5 |

TABLE I-continued

Chemical structure relationships of salicylanilide analogs tested for topical prophylaxis on mice for *Schistosoma mansoni* cercariae

| Walter Reed Number | Structure | Walter Reed Number | Structure |
|---|---|---|---|
| WR52606 | 2-HO, 5-Br-benzoyl-N-(4-bromophenyl)amide | WR54971 | 4-HO-benzoyl-N-(3,4-dichlorophenyl)amide |
| WR55787 | 3,5-dibromo-2-hydroxy-benzoyl-N-(4-(4-chlorophenylthio)phenyl)amide | WR56261 | 4-$O_2N$-benzoyl-N-(2-hydroxy-3-carboxy-5-sulfophenyl)amide |
| WR63260 | 2,4-dichloro-benzoyl-N-(3-chlorophenyl)amide | WR66707 | 2-HO-benzoyl-N-(3-chlorophenyl)amide |
| WR70432 | benzoyl-N-(3-bromophenyl)amide | WR70586 | 2-methyl-benzoyl-N-(2,4-dichlorophenyl)amide |
| WR71297 | 4-$O_2N$-benzoyl-N-(4-$N_2O$-phenyl)amide | WR78306 | 2-HO-benzoyl-N-(4-chlorophenyl)amide |
| WR78550 | 3,5-dibromo-2-hydroxy-benzoyl-N-(3-$CF_3$-phenyl)amide | WR78557 | 4-$O_2N$-benzoyl-N-(benzothiazolyl)amide |
| WR82188 | 2,4-dichloro-benzoyl-N-(1-naphthyl)amide | WR96544 | 2-OH,5-Cl-benzoyl-N-(2-hydroxy-5-chlorophenyl)amide |
| WR251249 | 2-hydroxy-naphthoyl-N-(2-chloro-4-NCS-phenyl)amide | WR251250 | 3,5-dibromo-2-hydroxy-benzoyl-N-(4-NCS-phenyl)amide |

TABLE II

The protective effect of salicylanilide analogs in methanol when applied to the tails of mice 24 hr before exposure to approximately 100 *Schistosoma mansoni* cercariae

| Walter Reed Number | Drug Concentration [W/V] | Unwashed Treatment Surface | | | Washed Treatment Surface | | |
|---|---|---|---|---|---|---|---|
| | | MWB of Test Mice | MWB of Control Mice | % Protection | MWB of Test Mice | MWB of Control Mice | % Protection |
| WR3216 | 1.0% | 0.2 ± 0.2 (5) | 46.5 ± 5.1 (5) | 99.6 | 0 (5) | 46.7 ± 6.0 (5) | 100 |
| WR3582 | 0.5% | 0 (5) | 55.3 ± 1.5 (5) | 100 | 0 (4) | 47.4 ± 3.0 (5) | 100 |
| WR13084 | 0.5% | 0 (5) | 46.5 ± 5.1 (5) | 100 | 0 (5) | 46.7 ± 6.0 (5) | 100 |
| WR17456 | 1.0% | 28.6 ± 3.5 (5) | 46.5 ± 5.1 (5) | 38.6 | 6.1 ± 2.2 (5) | 46.7 ± 6.0 (5) | 86.9 |
| WR25817 | 0.5% | 0 (5) | 55.5 ± 1.5 (5) | 100 | 0.8 ± 0.5 (5) | 47.4 ± 3.0 (5) | 98.3 |
| WR25818 | 1.0% | 0 (5) | 55.3 ± 1.5 (5) | 100 | 0 (5) | 47.4 ± 3.0 (5) | 100 |
| WR25819 | 0.5% | 0.8 ± 0.6 (5) | 55.3 ± 1.5 (5) | 98.5 | 0 (5) | 47.4 ± 3.0 (5) | 100 |
| WR54971 | 1.0% | 55.4 ± 3.8 (5) | 46.5 ± 5.1 (5) | 0 | 39.6 ± 3.7 (5) | 46.7 ± 6.0 (5) | 15.2 |
| WR63260 | 1.0% | 4.9 ± 2.5 (5) | 55.3 ± 1.5 (5) | 91.2 | 2.8 ± 1.6 (5) | 47.4 ± 3.0 (5) | 94 |
| WR70432 | 1.0% | 21.0 ± 4.9 (5) | 55.3 ± 1.5 (5) | 62.1 | 22.6 ± 3.6 (5) | 47.4 ± 3.0 (5) | 52.4 |
| WR70586 | 1.0% | 42.0 ± 5.4 (5) | 46.5 ± 5.1 (5) | 9.7 | 52.2 ± 5.3 (5) | 46.7 ± 6.0 (5) | 0 |
| WR78306 | 1.25% | 0 (5) | 46.7 ± 3.7 (4) | 100 | 0 (4) | 60.2 ± 2.0 (4) | 100 |
| WR81741 | 0.5% | 45.1 ± 1.7 (5) | 46.5 ± 5.1 (5) | 3.0 | 40.4 ± 5.6 (5) | 46.7 ± 6.0 (5) | 13.5 |

Note. MWB = The mean worm burdens of all the mice in the group. [W/V] = Percent weight of the drug per volume of vehicle. Results are ± standard error of the mean. Numbers in parentheses are the number of animals perfused in each experimental group. Washed = 30 min wash of the mouse tails with running tap water the day of drug treatment.

TABLE III

The protective effect of salicylanilide analogs in dimethyl sulfoxide when applied to the tails of mice 24 hr before exposure to approximately 100 *Schistosoma mansoni* cercariae

| Walter Reed Number | Drug Concentration [W/V] | Unwashed Treatment Surface | | | Washed Treatment Surface | | |
|---|---|---|---|---|---|---|---|
| | | MWB of Test Mice | MWB of Control Mice | % Protection | MWB of Test Mice | MWB of Control Mice | % Protection |
| WR593 | 1.25% | 0 (5) | 48.7 ± 6.6 (5) | 100 | 0 (5) | 36.6 ± 3.8 (5) | 100 |
| WR10019 | 1.25% | 1.8 ± 1.8 (5) | 53.4 ± 2.3 (5) | 96.6 | 23.2 ± 6.8 (4) | 43.1 ± 7.6 (5) | 46.3 |
| WR34912 | 1.25% | 0 (4) | 53.4 ± 2.3 (5) | 100 | 0 (5) | 43.1 ± 7.6 (5) | 100 |
| WR39958 | 0.5% | 0 (5) | 42.5 ± 7.4 (5) | 100 | 0 (5) | 47.8 ± 2.4 (5) | 100 |
| WR39960 | 1.0% | 0 (5) | 34.7 ± 2.7 (5) | 100 | 28.0 ± 2.2 (5) | 42.0 ± 3.3 (5) | 33.3 |
| WR41252 | 1.0% | 0 (5) | 44.0 ± 1.9 (4) | 100 | 0 (5) | 49.4 ± 3.2 (5) | 100 |
| WR42406 | 1.0% | 30.0 ± 5.1 (5) | 44.0 ± 1.9 (4) | 31.8 | 45.2 ± 14.4 (5) | 49.4 ± 3.2 (5) | 8.6 |
| WR47332 | 1.0% | 0.4 ± 0.4 (5) | 42.5 ± 7.4 (5) | 99.1 | 2.8 ± 1.6 (3) | 47.8 ± 2.4 (5) | 94.1 |
| WR52606 | 1.25% | 0 (5) | 37.2 ± 3.8 (5) | 100 | Not Done | Not Done | |
| WR55787 | 1.0% | 0 (5) | 46.9 ± 1.5 (5) | 100 | 0 (3) | 44.2 ± 6.3 (5) | 100 |
| WR56261 | 1.0% | 49.1 ± 0 (2) | 42.5 ± 7.4 (5) | 0 | 38.9 ± 8.2 (5) | 47.8 ± 2.4 (5) | 18.6 |
| WR66707 | 1.0% | 0 (5) | 44.0 ± 1.9 (4) | 100 | 0 (5) | 49.4 ± 3.2 (5) | 100 |
| WR71297 | 1.0% | 41.4 ± 2.8 (5) | 42.5 ± 7.4 (5) | 2.7 | 41.1 ± 5.5 (4) | 47.8 ± 2.4 (5) | 14.0 |
| WR78550 | 1.25% | 0 (3) | 53.4 ± 2.3 (5) | 100 | 0 (5) | 43.1 ± 7.6 (5) | 100 |
| WR78557 | 1.0% | 43.9 ± 7.7 (4) | 42.5 ± 7.4 (5) | 0 | 43.4 ± 7.9 (3) | 47.8 ± 2.4 (5) | 9.1 |
| WR81231 | 1.0% | 0 (5) | 34.7 ± 2.7 (5) | 100 | 39.2 ± 2.1 (4) | 42.2 ± 3.3 (5) | 6.7 |
| WR81795 | 0.5% | 40.0 ± 4.9 (5) | 44.0 ± 1.9 (4) | 9.1 | 41.7 ± 3.8 (5) | 49.4 ± 3.2 (5) | 15.6 |
| WR81800 | 0.5% | 49.8 ± 5.0 (5) | 44.0 ± 1.9 (4) | 0 | 56.7 ± 2.9 (5) | 49.4 ± 3.2 (5) | 0 |
| WR81801 | 0.5% | 15.4 ± 5.7 (4) | 44.0 ± 1.9 (4) | 65.0 | 24.8 ± 7.5 (5) | 49.4 ± 3.2 (5) | 49.8 |

TABLE III-continued

The protective effect of salicylanilide analogs in dimethyl sulfoxide when applied to the tails of mice 24 hr before exposure to approximately 100 *Schistosma mansoni* cercariae

| Walter Reed Number | Drug Concentration [W/V] | Unwashed Treatment Surface | | | Washed Treatment Surface | | |
|---|---|---|---|---|---|---|---|
| | | MWB of Test Mice | MWB of Control Mice | % Protection | MWB of Test Mice | MWB of Control Mice | % Protection |
| WR81802 | 1.0% | 43.3 ± 4.0 (5) | 44.0 ± 1.9 (4) | 1.6 | 47.7 ± 2.9 (5) | 49.4 ± 3.2 (5) | 3.5 |
| WR81803 | 1.0% | 33.7 ± 6.2 (4) | 44.0 ± 1.9 (4) | 23.5 | 53.5 ± 7.6 (5) | 49.4 ± 3.2 (5) | 0 |
| WR82188 | 1.0% | 55.3 ± 9.7 (5) | 42.5 ± 7.4 (5) | 0 | 34.2 ± 5.9 (4) | 47.8 ± 2.4 (5) | 28.4 |
| WR96544 | 1.0% | 0 (5) | 47.6 ± 2.2 (5) | 100 | 0 (4) | 50.4 ± 10.4 (5) | 100 |
| WR251249 | 1.0% | 5.5 ± 1.7 (5) | 46.9 ± 1.5 (5) | 88.3 | 3.8 ± 0.9 (5) | 44.2 ± 6.3 (5) | 4 |
| WR251250 | 1.0% | 0 (5) | 46.9 ± 1.5 (5) | 100 | 0 (5) | 44.2 ± 6.3 (5) | 100 |

Note: MWB = The mean worm burdens of all the mice in the group. [W/V] = Percent weight of the drug per volume of vehicle. Results are ± standard error of the mean. Numbers in parentheses are the number of animals perfused in each experimental group. Washed = 30 min wash of the mouse tails with running tap water the day of drug treatment.

TABLE IV

The protective effect of a salicylanilide analog in isopropanol when applied to the tails of mice 24 hours before exposure to approximately 100 *Schistosoma mansoni* cercariae

| Walter Reed Number | Drug Concentration [W/V] | Unwashed Treatment Surface | | | Washed Treatment Surface | | |
|---|---|---|---|---|---|---|---|
| | | MWB of Test Mice | MWB of Control Mice | % Protection | MWB of Test Mice | MWB of Control Mice | % Protection |
| WR46234 | 0.3% | 0 (5) | 35.7 ± 5.8 (4) | 100 | 0 (5) | 30.2 ± 3.0 (4) | 100 |

Note: MWB = The mean worm burdens of all the mice in the group. [W/V] = Percent weight of the drug per volume of vehicle. Results are ± standard error of the mean. Numbers in parentheses are the number of animals perfused in each experimental group. Washed = 30 min wash of the mouse tails with running tap water the day of drug treatment.

TABLE V

The protective effect of salicylanilide analogs in ethanol when applied to the tails of mice 24 hours before exposure to approximately 50 radio-labelled *Schistosoma mansoni* cercariae

| Walter Reed Number | Drug Concentration [W/V] | Mean cercariae Counts in Test Mice | Mean cercariae Counts in Control Mice | Percent Protection |
|---|---|---|---|---|
| WR593 | 0.25% | 0 (3) | 25.9 ± 2.4 (10) | 100 |
| WR34912 | 0.156% | 0 (3) | 25.9 ± 2.4 (10) | 100 |
| WR46234 | 0.156% | 0 (3) | 25.9 ± 2.4 (10) | 100 |

Note: [W/V] = Percent weight of the drug per volume of vehicle. Results are ± standard error of the mean. Numbers in parentheses are the number of animals. The tails of all mice were washed 30 min with running tap water the day of drug treatment. *Schistosoma mansoni* intermediate host is *Biomphalaria glabrata*.

TABLE VI

The protective effect of salicylanilide analogs in ethanol when applied to the abdomens of mice 24 hours before exposure to approximately 50 radio-labelled *Gigantobilharzia* cercariae

| Walter Reed Number | Drug Concentration [W/V] | Mean cercariae Counts in Test Mice | Mean cercariae Counts in Control Mice | Percent Protection |
|---|---|---|---|---|
| WR46234 | 1.0% | 0 (10) | 3.6 ± 0.7 (10) | 100 |

Note: [W/V] = Percent weight of the drug per volume of vehicle. Results are ± standard error of the mean. Numbers in parentheses are the number of animals. The abdomens of all mice were washed 10 min with running tap water the day of drug treatment. *Gigantobilharzia huronensis* intermediate host is *Physa gyrina*.

We claim:

1. A method for preventing shistosomal infections in an animal exposed to schistosome-infested water which comprises applying to the skin of said animal prior to exposure of the skin to the schistosome-infested water a composition comprising a 2-hydroxy-benzoic anilide selected from the compounds represented by the formula

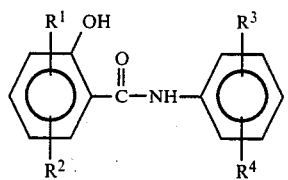

wherein $R^1$ is hydrogen, Cl, Br, I or F; $R^2$ is $NO_2$, Cl, Br, I or F; $R^3$ is hydrogen, hydroxy, Cl, Br, I, F, alkyl (having 1 to 3 carbon atoms),

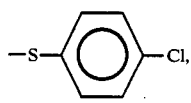

$CF_3$; and $R^4$ is $NO_2$, NCS or $R^3$ is an amount sufficient to achieve an antipenetrant effect against cercaria of infectious schistosome parasites.

2. The method of claim 1 wherein said infectious schistosome parasites are selected from the group consisting essentially of species of the genera Schistosoma, Trichobilharzia, Ornithobilharzia, Microbilharzia, Gigantobilharzia and Schistosomatium.

3. The method of claim 2 wherein $R^1$ is hydrogen, Cl, Br, or I; $R^2$ is $NO_2$, NCS, or is selected from the group of radicals listed for $R^1$; $R^3$ is hydroxy, hydrogen, Cl, Br, $CH_3$,

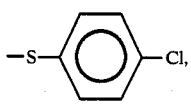

$CF_3$; and $R^4$ is $NO_2$, NCS, or selected from the group of radicals listed for $R^3$.

4. The method of claim 3 wherein the 2-hydroxy-benzoic anilide is selected from the compounds selected from the group consisting of,

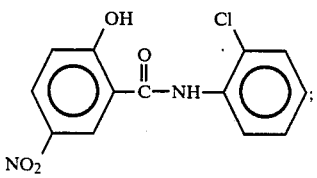

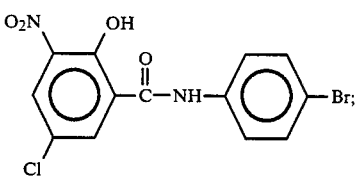

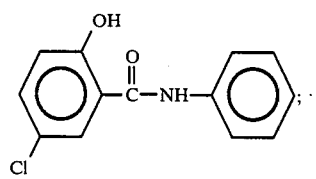

-continued

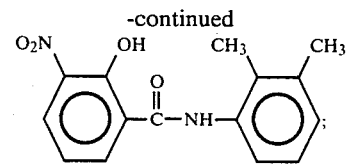

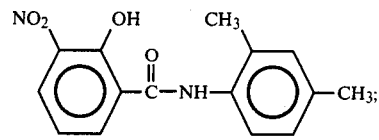

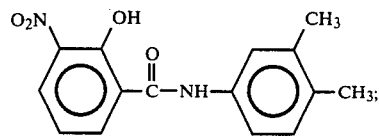

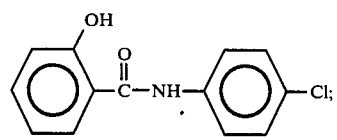

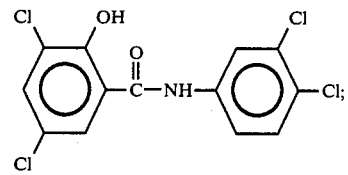

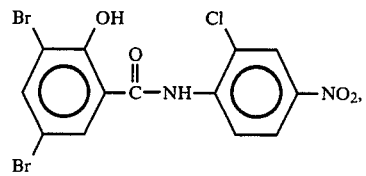

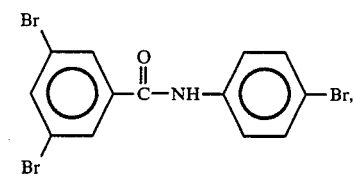

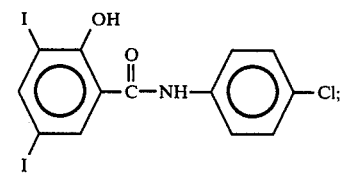

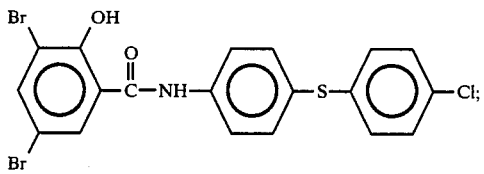

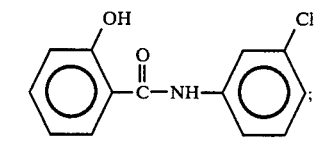

-continued

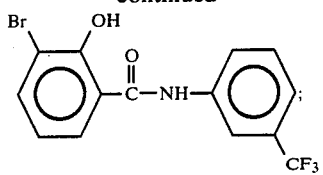

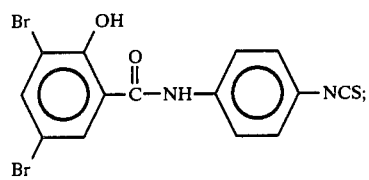

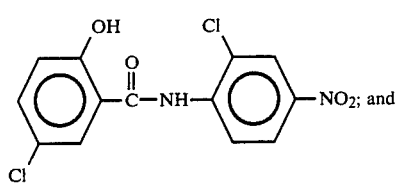

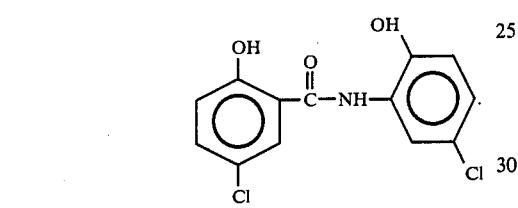

5. The method of claim 4 wherein the 2-hydroxy-benzoic anilide is

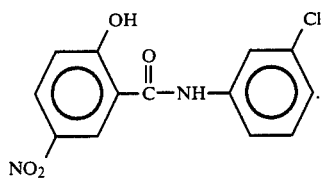

6. The method of claim 4 wherein the 2-hydroxy-benzoic anilide is

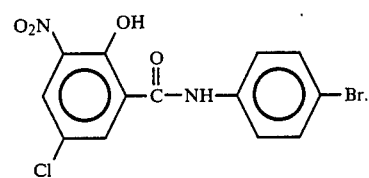

7. The method of claim 4 wherein the 2-hydroxy-benzoic anilide is

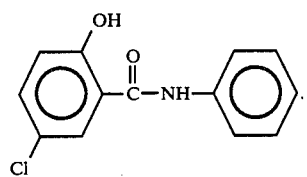

8. The method of claim 4 wherein the 2-hydroxy-benzoic anilide is

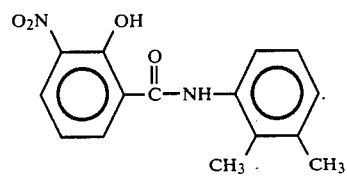

9. The method of claim 4 wherein the 2-hydroxy-benzoic anilide is

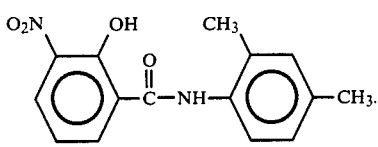

10. The method of claim 4 wherein the 2-hydroxy-benzoic anilide is

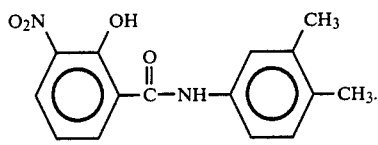

11. The method of claim 4 wherein the 2-hydroxy-benzoic anilide is

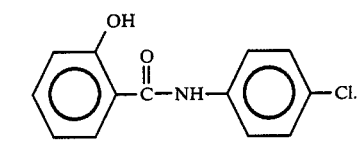

12. The method of claim 4 wherein the 2-hydroxy-benzoic anilide is

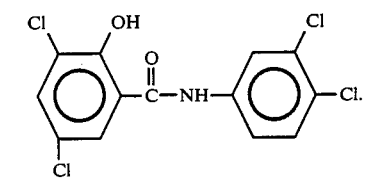

13. The method of claim 4 wherein the 2-hydroxy-benzoic anilide is

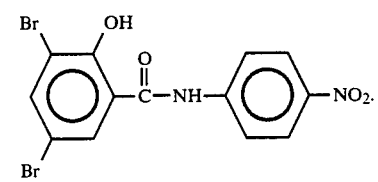

14. The method of claim 4 wherein the 2-hydroxy-benzoic anilide is

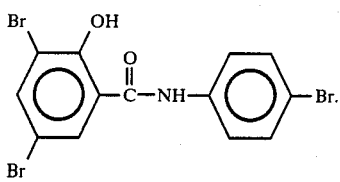

15. The method of claim 4 wherein the 2-hydroxybenzoic anilide is

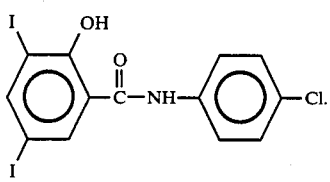

16. The method of claim 4 wherein the 2-hydroxybenzoic anilide is

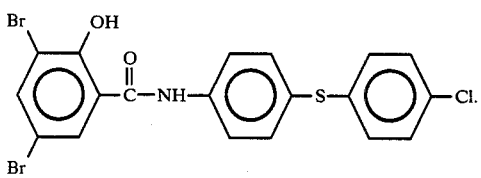

17. The method of claim 4 wherein the 2-hydroxybenzoic anilide is

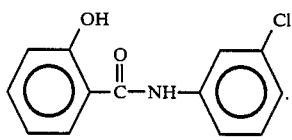

18. The method of claim 4 wherein the 2-hydroxybenzoic anilide is

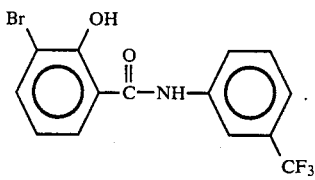

19. The method of claim 4 wherein the 2-hydroxybenzoic anilide is

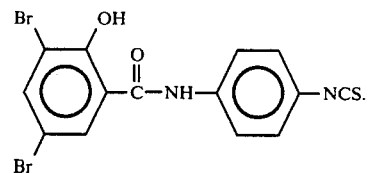

20. The method of claim 4 wherein the 2-hydroxybenzoic anilide is

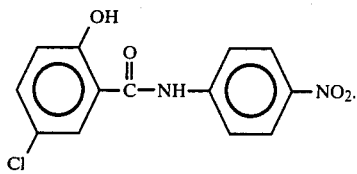

21. The method of claim 4 wherein the 2-hydroxybenzoic anilide is

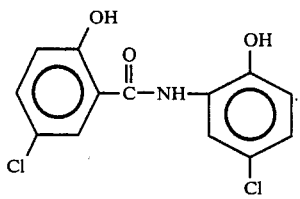

22. The method of claim 4 wherein the schistosome parasite is Schistosoma spp.
23. The method of claim 22 wherein the schistosome is *Schistosoma mansoni.*
24. The method of claim 22 wherein the schistosome is *Schistosoma japonicum.*
25. The method of claim 22 wherein the schistosome is *Schistosoma haematobium.*
26. The method of claim 22 wherein the schistosomal infection is schistosome cercarial dermatitis.
27. The method of claim 26 wherein the form of schistosome cercarial dermatitis is selected from the group consisting essentially of species of the genera Trichobilharzia, Ornithobilharzia, Schistosoma, Microbilharzia, Gigantobilharzia and Schistosomatium.
28. The method of claim 1 wherein the 2-hydroxybenzoic anilide composition contains an organic vehicle selected from the group consisting essentially of methanol, ethanol, dimethylsulfoxide and isopropanol.
29. The method of claim 28 wherein the organic vehicle is ethanol.
30. The method of claim 4 wherein the schistosome parasite is selected from the group consisting essentially of species of the genera Trichobilharzia, Ornithobilharzia, Schistosoma, Gigantobilharzia, Schistosomatium and Microbilharzia.
31. The method of claim 30 wherein the schistosome parasite is *Gigantobilharzia huronensis.*

* * * * *